(12) United States Patent
Nemoto

(10) Patent No.: US 7,503,906 B2
(45) Date of Patent: *Mar. 17, 2009

(54) SYRINGE BARREL AND CYLINDER HOLDER

(75) Inventor: Shigeru Nemoto, Tokyo (JP)

(73) Assignee: Nemoto Kyorindo Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/119,423

(22) Filed: May 12, 2008

(65) Prior Publication Data

US 2008/0317638 A1    Dec. 25, 2008

Related U.S. Application Data

(60) Continuation of application No. 10/781,124, filed on Feb. 18, 2004, now abandoned, which is a division of application No. 10/211,099, filed on Jul. 31, 2002, now abandoned.

(30) Foreign Application Priority Data

Aug. 1, 2001    (JP)    ............................ 2001-233604

(51) Int. Cl.
    *A61M 1/00*    (2006.01)
(52) U.S. Cl. ...................................................... 604/151
(58) Field of Classification Search ............ 128/DIG. 1, 128/12, 13; 604/131, 150–6
    See application file for complete search history.

(56) References Cited

U.S. PATENT DOCUMENTS 5,947,929 A * 9/1999 Trull ........................... 604/152
6,569,127 B1 * 5/2003 Fago et al. ................... 604/218
6,958,053 B1 * 10/2005 Reilly ......................... 604/154

* cited by examiner

*Primary Examiner*—Kevin C Sirmons
*Assistant Examiner*—Catherine N Witczak
(74) *Attorney, Agent, or Firm*—Knobbe Martens Olson & Bear LLP

(57) ABSTRACT

An arcuate guide projection is provided on a front surface of a flange of a syringe barrel and an arcuate guide groove for guiding the guide projection is provided on a front sidewall surface of a flange insert groove of a cylinder holder. When the syringe is mounted, the guide projection and the guide groove are brought into engagement thereby preventing the flange from slipping off upwardly.

9 Claims, 16 Drawing Sheets

(a)

F-F cross section (Enlarged view: shape of projection)

(b)

C-C cross section and E-E cross section (Enlarged view: shape of projection)

(b)

(a)

(a)        (b)

(a)

(b)

A-A cross section

SYRINGE BARREL AND CYLINDER HOLDER

This application is a continuation of U.S. patent application Ser. No. 10/781,124 filed on Feb. 18, 2004, which application is a divisional of U.S. patent application Ser. No. 10/211,099 filed on Jul. 31, 2002 and also claims foreign priority to Japanese Patent Application No. 2001-233604, filed Aug. 1, 2001.

FIELD OF THE INVENTION

The present invention relates to a syringe and a cylinder holder which are suitable for injection at high injection pressure using a driving mechanism such as an automatic injection device.

DESCRIPTION OF THE RELATED ART

Syringes are used for injection of liquid in various fields typically including a medical field. Injection of a chemical solution having high viscosity such as a contrast agent for X ray CT imaging and a contrast agent for MRI (magnetic resonance imaging apparatus) requires high pressure, causes difficulty in manual handling, and makes intense jobs. Therefore, it is general to effect injection using a mechanical syringe driving mechanism such as an automatic injection apparatus and the like. FIG. 13 shows a syringe 20 to be mounted on such an automatic injecting apparatus 10. The automatic injecting apparatus 10 comprises a cylinder holder 11, a piston holder 12, and a motor inside (not shown), and the cylinder holder 11 fixes a syringe barrel 21 by holding a flange 22 and the piston holder 12 holds a piston flange 24. A piston 23 can be moved relative to the syringe barrel 21 by progressing or regressing the piston holder 12 by a motor, to effect injection (discharge of liquid from the syringe) or suction of liquid. FIG. 14 shows the syringe 20 mounted on the automatic injecting apparatus 10.

Further, as shown in FIG. 15, when a syringe of smaller size is mounted on this automatic injecting apparatus, the syringe barrel 21 is mounted on a dismountable adaptor 13 (functions as a cylinder holder for the syringe) which is further mounted on the automatic injecting apparatus 10. FIG. 16 shows the syringe 20 mounted on the automatic injecting apparatus 10.

FIG. 18 provides detailed drawings of the adaptor 13 ((a) is a plan view, and (b) is a rear side view)). The syringe barrel 21 can be held by fitting the flange 22 of the syringe barrel 21 into a flange insertion groove 14 of the adaptor 13. For the mounting, as shown in FIG. 17(a), the flange 22 is fitted into the flange groove 14 while directing a flange cut portion 25 vertically. Then, the flange is rotated by 90° to be fixed so that it is not disconnected. FIG. 17(b) is a view showing the rotating process, and FIG. 17(c) is a view showing the use position.

In the operational position, the arc of the flange is engaged with the arc of the flange insert groove so as not to slip off in the upward direction. However, to prevent the slip-off, it is necessary to secure a certain level of the arc length of the flange insert groove and therefore the opening length of the flange insert groove cannot be made large. At the time of mounting the syringe, if the difference between the opening length L' and the length of the flange cut part W can not be made large as shown in FIG. 17(a), the mounting operation will need time and effort.

Further, the flange thickness and the flange insertion groove width are so designed to give slight clearance between the flange and flange groove for enabling smooth mounting of the syringe barrel. The reason for this design is also that if the clearance is designed to zero completely, mounting may be sometimes impossible due to certain extent production error to be taken into consideration because the syringe barrel and the cylinder holder (including the adaptor) are usually formed of different materials. Consequently, slight backlash and play in mounted condition is inevitable. However, if there is an error in the mounting procedure, the syringe may sometimes be raised from the right position. If injection of a contrast agent and chemical solution is conducted when fitting in such slight clearance is displaced, the piston shall be pushed under condition in which the flange 22 is inclined relative to the flange insertion groove 14, as shown schematically in FIG. 19, and the total pressure is concentrated only on a part of the flange, and resultantly, in the worst case, the flange may be occasionally broken particularly from the base part.

SUMMARY OF THE INVENTION

The present invention has been achieved in view of the above described problems, and its object is to provide a syringe barrel a cylinder holder, where the syringe is not easily broken in injecting liquid of high viscosity at high pressure and can be easily mounted.

An aspect of the present invention is directed to a syringe barrel, comprising a guide projection on a front surface of a flange.

The syringe barrel may further comprise a press projection formed on the rear surface of the flange; a tip of the press projection being capable of compressed to press the flange against a front sidewall surface of a flange insert groove when the flange is inserted into the flange insert groove formed in a cylinder holder and is fitted in a use position.

Another aspect of the present invention is directed to a cylinder holder for holding a syringe barrel having a flange, the syringe barrel comprising a guide projection on a front surface of the flange, the cylinder holder comprising: a flange insert groove for holding a flange of a syringe barel and a guide groove formed on a front sidewall surface of the flange insert groove; the guide groove being capable of guiding a guide projection formed on a front surface of a flange of a syringe barrel.

In the present invention, the guide projection is preferably formed in arcuate shape. Also, the guide groove is preferably formed in arcuate shape. "Arcuate shape" generally means that at least a portion of one line of outward form is a part of a circle. In the preferred embodiments, portions of two lines opposite to each other are the parts of concentric circles. The examples will be described by showing the embodiments.

The above-mentioned syringe barrel and the above-mentioned cylinder holder may be used in combination for a chemical solution injection system.

The above described syringe barrel may be used in combination with a syringe piston for a pre-filled syringe filled with a chemical solution. The chemical solution may include a contrast medium.

In the present invention, the term "cylinder holder" means one which can hold a syringe barrel by a groove, and when a syringe barrel is mounted on an adaptor before being set in an injecting apparatus, the term "cylinder holder" is construed to include such adaptor. The cylinder holder is usually incorporated in an automatic injecting apparatus, or integrated with an automatic injecting apparatus as one body.

DESCRIPTION OF SYMBOLS

Figure 1:
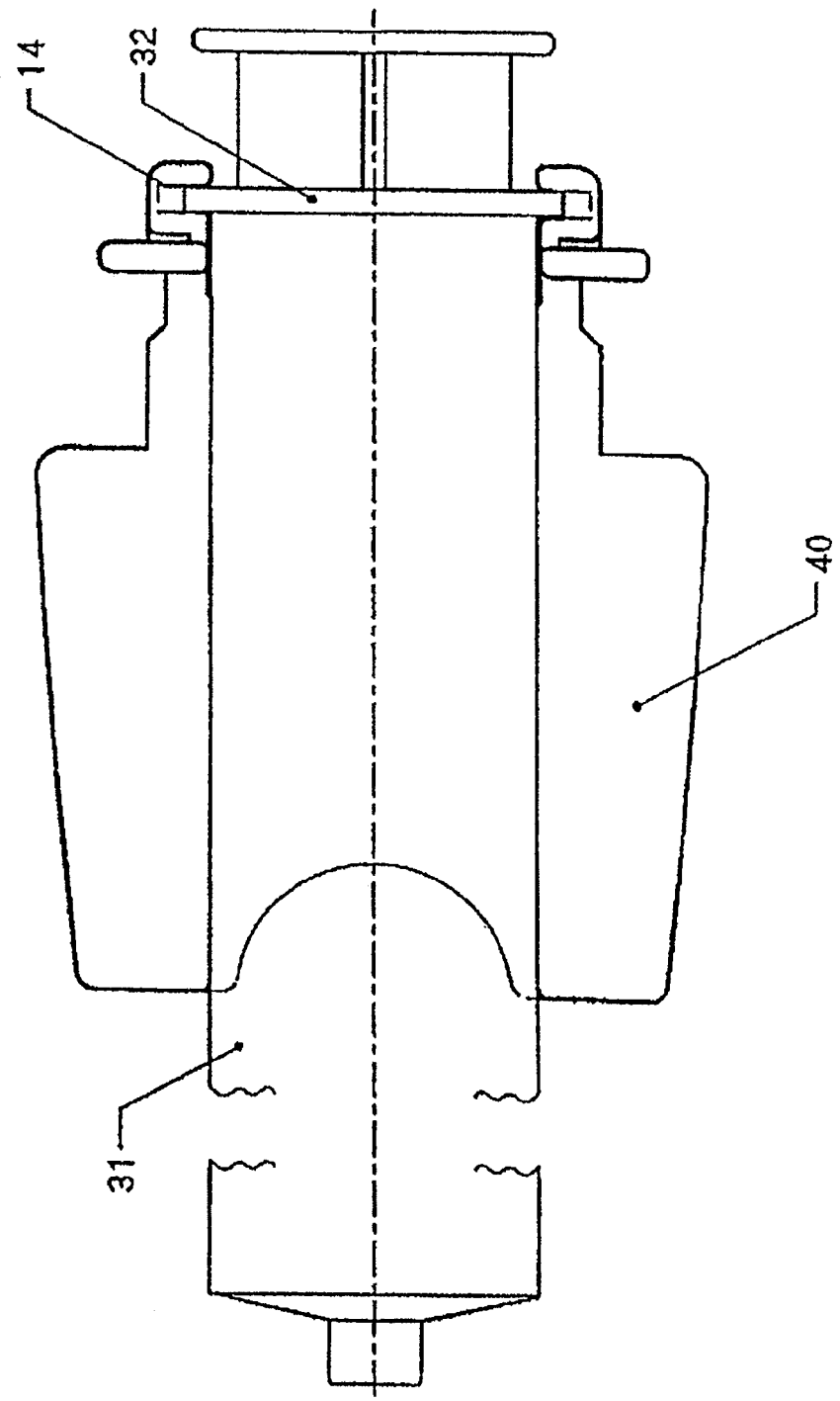
FIG. 1 shows the state in which a syringe barrel is mounted on a cylinder holder.

10 . . . automatic injection device
11 . . . cylinder holder
12 . . . piston holder
13 . . . adaptor
14 . . . flange insert groove
21 . . . syringe barrel
22 . . . flange
23 . . . piston
24 . . . piston flange
25 . . . flange cut part
31 . . . syringe barrel
32 . . . flange
33, 33a, 33b . . . guide projection
34, 34a to 34d . . . guide projection
40 . . . adaptor
41 . . . guide groove
42 . . . guide groove
51 . . . press projection
52 . . . reinforcing rib
52a . . . radial part of reinforcing rib
52b . . . concentric part of reinforcing rib

DETAILED DESCRIPTION OF THE INVENTION

Figure 2:
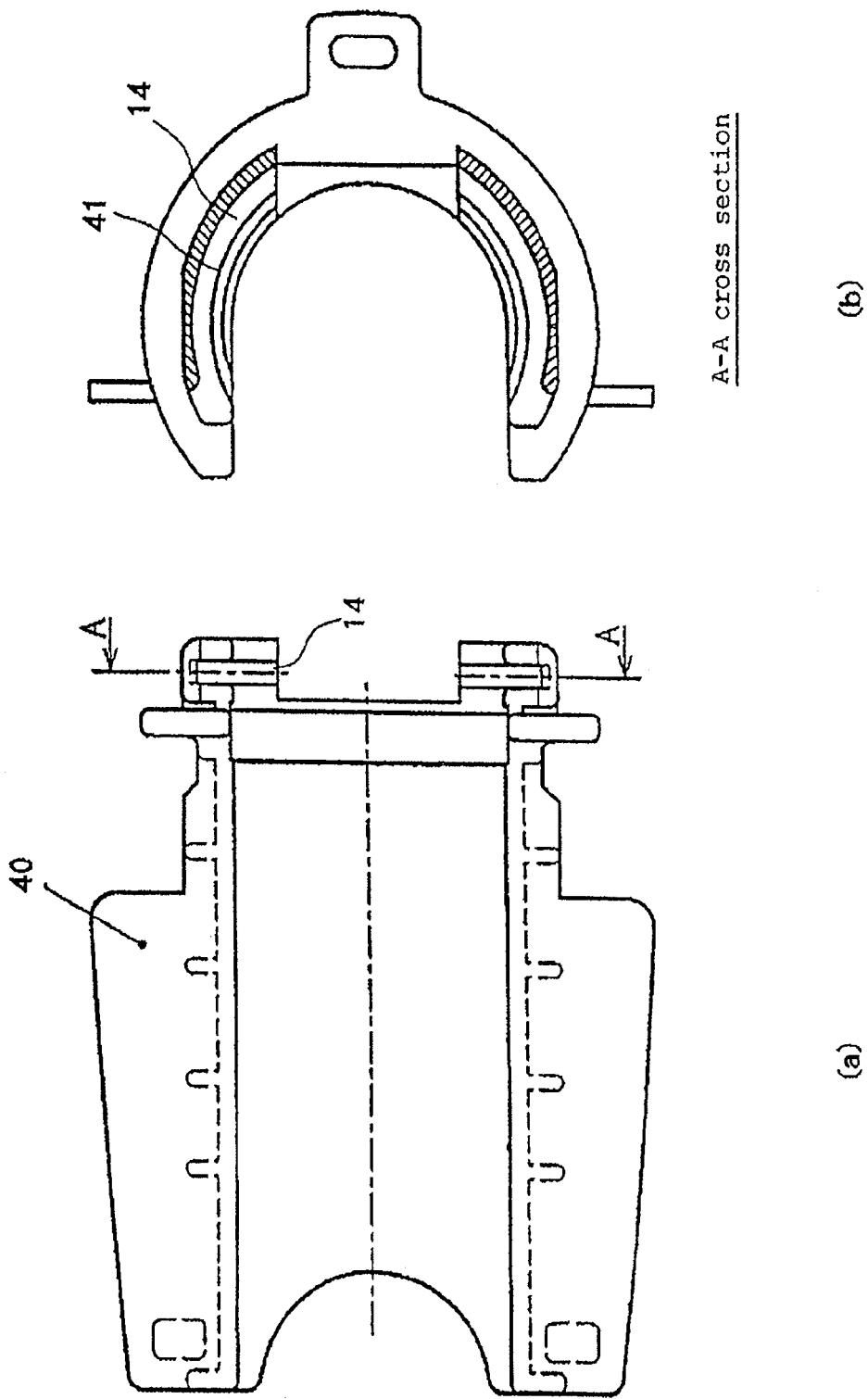
FIG. 2 shows an adaptor (cylinder holder), wherein (a) is a plan view from a mounting direction of the syringe, and (b) is a side cross sectional view in which an A-A cross section of (a) is seen from rear side.
Figure 3:
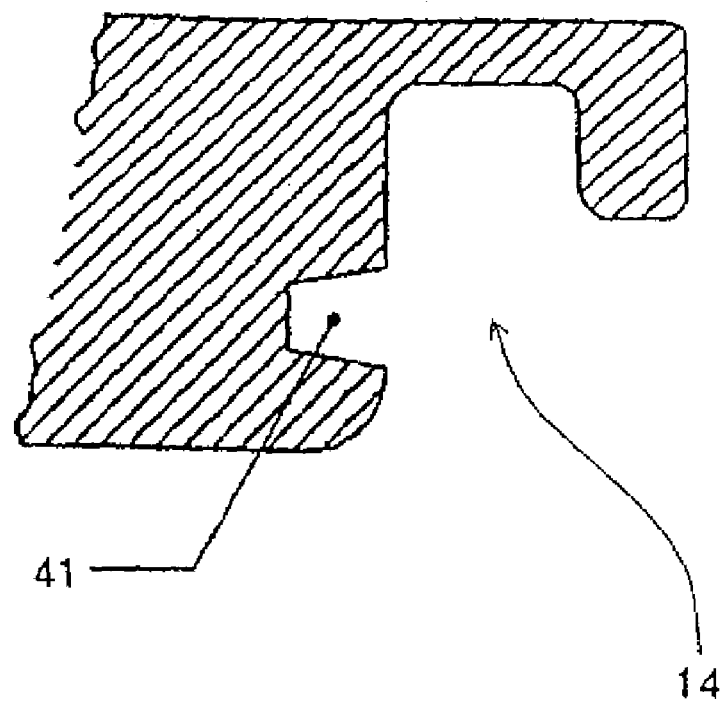
FIG. 3 is a cross sectional view of a flange insert groove of an adaptor.

FIG. 1 shows the state in which a flange 32 of a syringe barrel 31 is fitted in a flange insert groove 14 of an adaptor 40 (cylinder holder). FIG. 2 shows the adaptor 40 in which FIG. 2(a) is a plan view seen from an attaching direction of the syringe barrel and FIG. 2(b) is an A-A cross section in FIG. 2(a) viewed from rear side. FIG. 3 is an enlarged cross sectional view of a portion of the flange insert groove 14. A guide groove 41 is formed in an arcuate shape on a front sidewall surface of the flange insert groove 14 provided in the adaptor.

Figure 4:
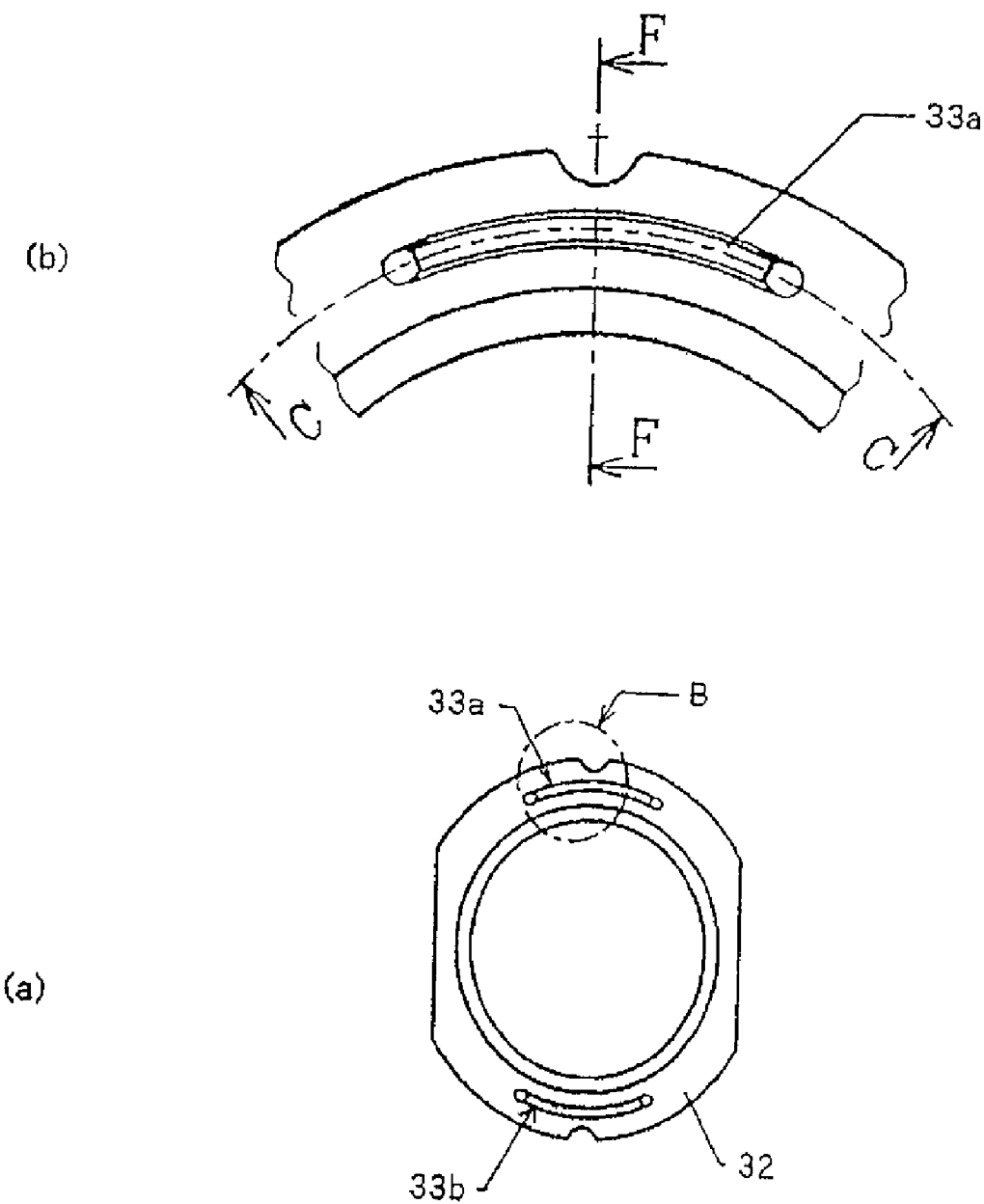
FIG. 4 is a side view of the flange surface of a syringe barrel seen from a front side, wherein
 (a) shows a frontal view (whole view) of the flange, and
 (b) shows an enlarged view of part B of (a).
Figure 5:
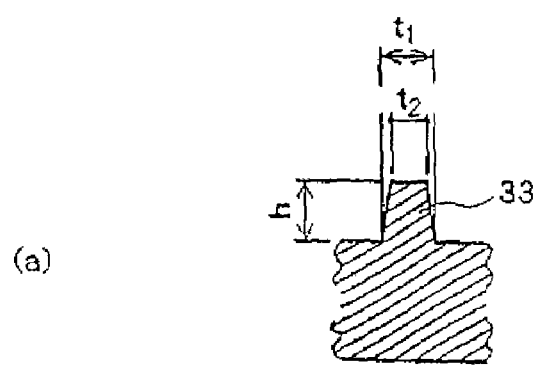
FIG. 5 is a cross sectional view of a syringe, wherein
 (a) shows an F-F cross section of FIGS. 4 and 11,
 (b) shows a C-C cross section of FIG. 4 and an E-E cross section of FIG. 11.
Figure 5:
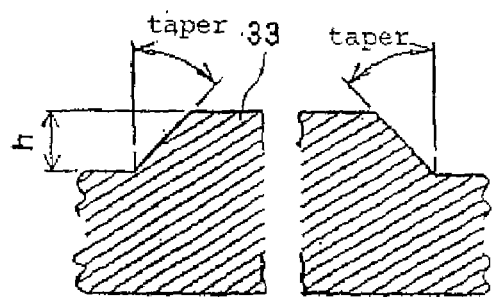

In the meantime, FIG. 4 shows the flange of the syringe barrel, which is used together with the adaptor, viewed from the tip side of the syringe ((a) is a whole view of the front surface and (b) is an enlarged view of the part B of (a)). As shown in this drawing, the front surface of the flange 32 is provided with arcuate guide projections 33 (33a, 33b). An F-F cross section of FIG. 4 is shown in FIG. 5(a), and a C-C cross section in FIG. 5(b). As shown in the cross sectional view of FIG. 5(a), the guide projection 33 of this embodiment has a cross section shape in accordance with the guide groove 41 of the adaptor and an arcuate shape in the lengthwise direction, and is adapted to be able to rotate along the guide groove 41 of the adaptor. It is preferable to form the end portion of the guide projection in a longitudinal direction in a tapered shape as shown in FIG. 5(b) so as to be smoothly guided into the guide groove.

Figure 6:
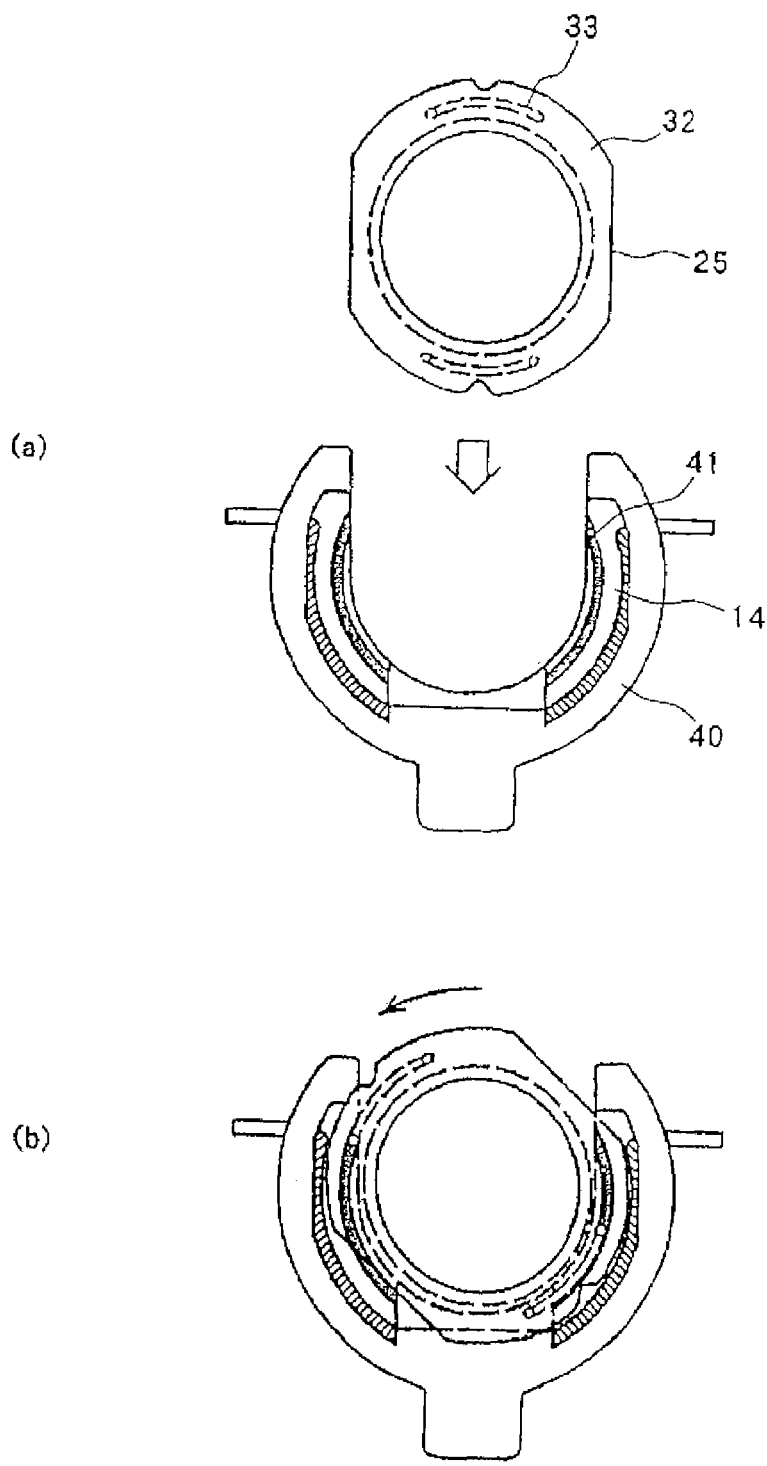
FIG. 6 schematically shows the state of mounting a syringe on an adaptor, wherein
 (a) shows a state before mounting, and
 (b) shows a state after mounting, of being rotated partway to a fixing location.

FIG. 6 is a cross sectional view of the flange insert groove seen from rear side showing the mounting of the syringe barrel onto the adaptor. First, as shown in FIG. 6(a), the flange 32 is inserted into the flange insert groove 14 while keeping the flange cut part 25 substantially vertical. Thereafter, as shown in FIG. 6(b), the guide projection 33 is rotated while being fitted in the guide groove 41 until it reaches the use position.

Figure 7:
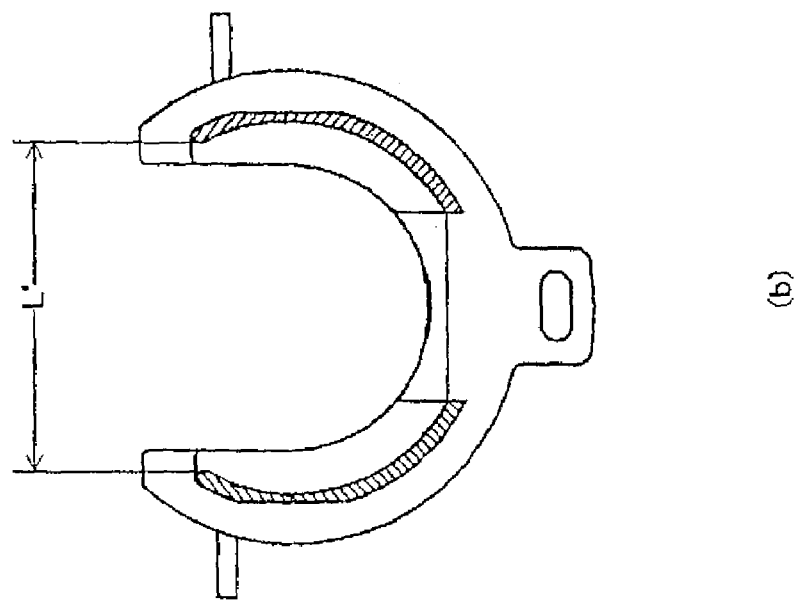
FIG. 7 shows a comparison between an opening length of an adaptor of the present invention and that of a conventional one, wherein
 (a) shows an adaptor of the present invention, and
 (b) shows a conventional adaptor.
Figure 7:
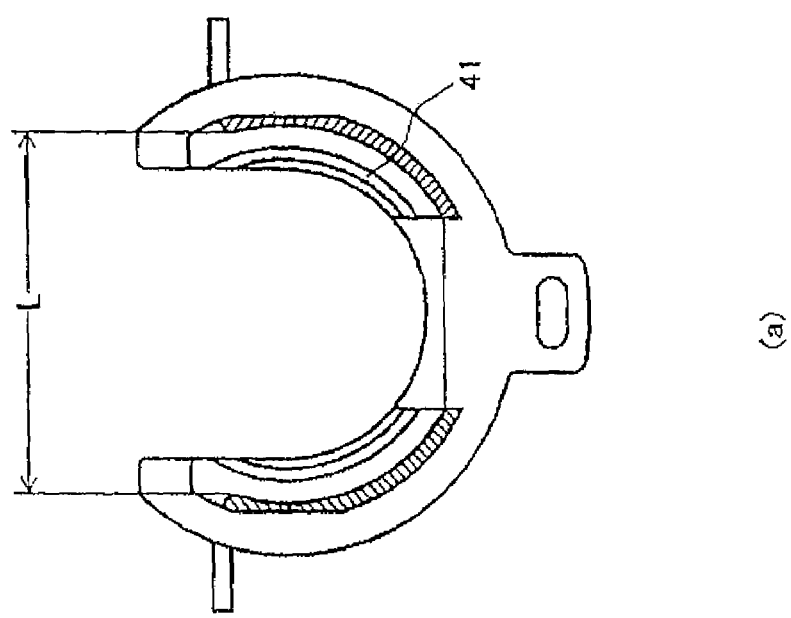
Figure 17:
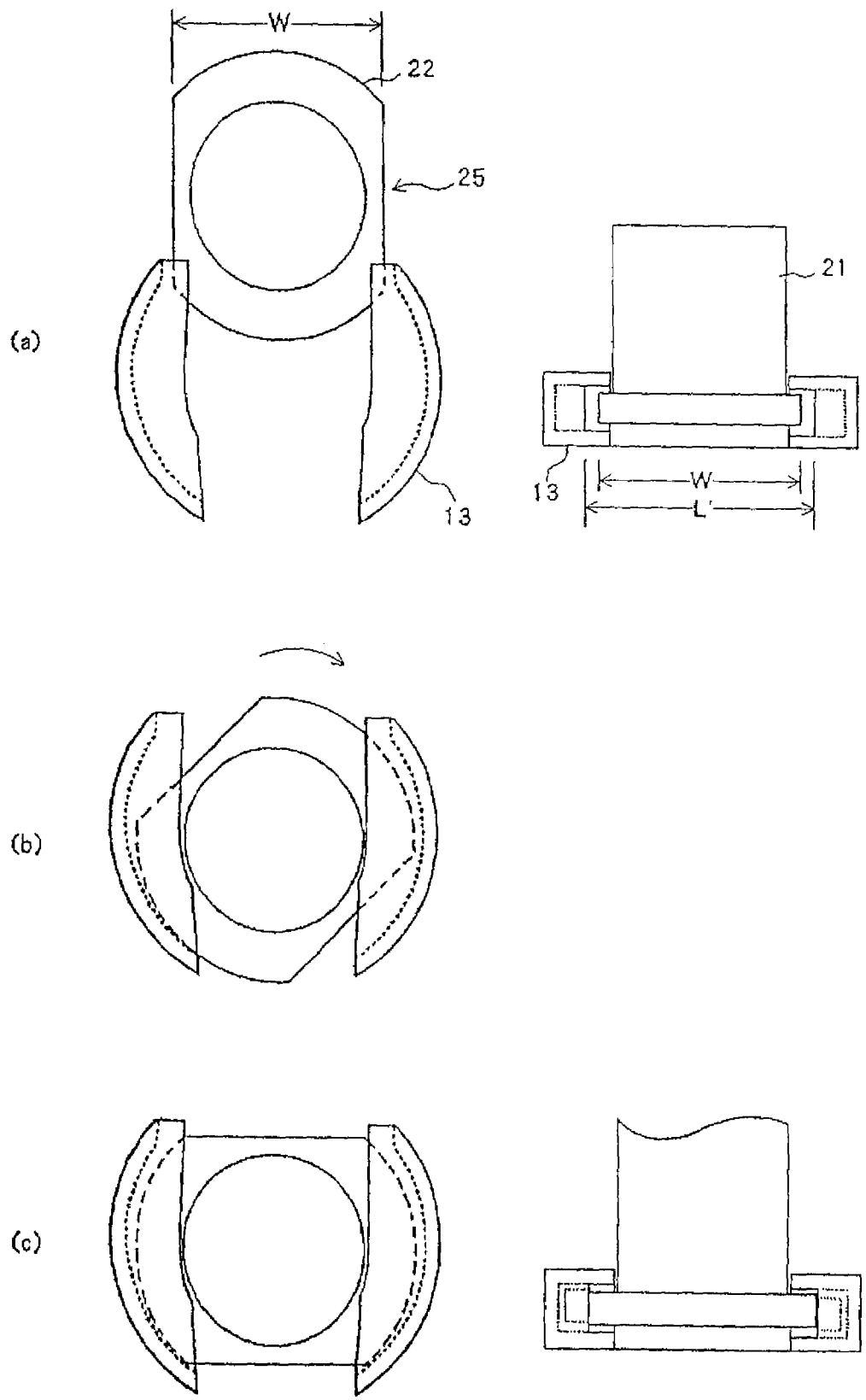
FIG. 17 schematically shows holding and positioning of a syringe by means of the cylinder holder (adaptor) of the automatic injection device shown in FIGS. 13 and 15.
Figure 18:
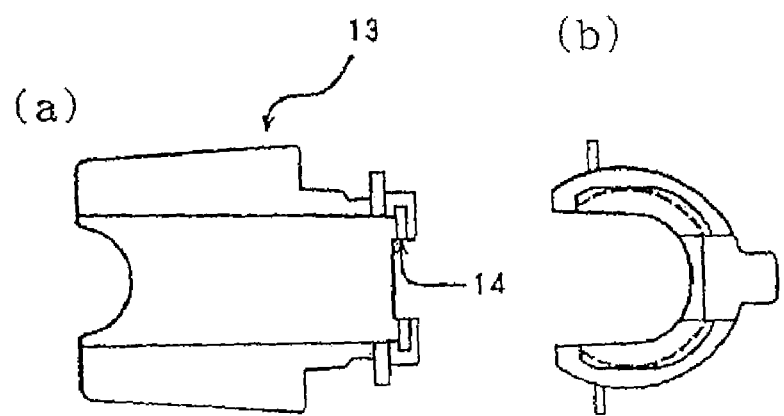
FIG. 18 is an enlarged view of an adaptor.
Figure 19:
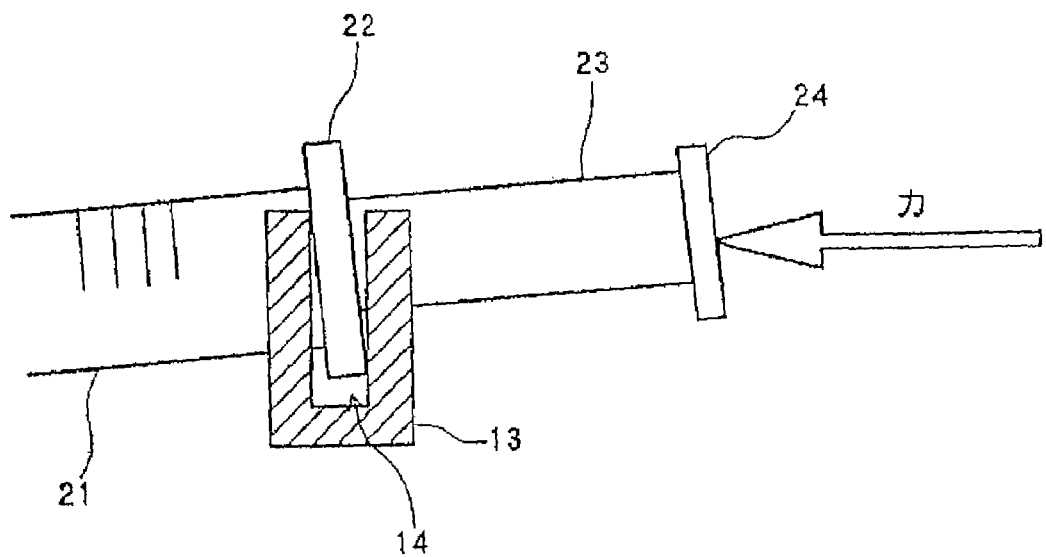
FIG. 19 schematically shows a state in which the flange of a syringe barrel is displaced floating up from the cylinder holder.

Referring to FIG. 7, the opening length of the flange groove will be described. FIG. 7(b) is a conventional adaptor; since it has no guide groove, the arc part of the groove needs to be made large to prevent the flange from slipping out upwardly. For this reason, the opening L' can only be slightly larger than the length of the flange in the flange cut part direction W (see FIG. 17). On the other hand, since the adaptor of the present invention shown in FIG. 7(a) can prevent the upward slip off with the guide groove 41, the arc part of the groove can be made short. As a result, the opening length L can be made large and thereby facilitating the mounting operation of the syringe. As a matter of course, the adaptor of the present invention may be arranged such that the length of the arc part of the flange insert groove is as long as those of conventional types to prevent the slipping off of the syringe more securely. But, for general uses, it is preferable to make the opening length large placing higher priority on the operational convenience and workability.

There are no particular restrictions on the cross section shapes of the guide projection and the guide groove of the adaptor as long as they fit with each other easily and the syringe will not slip off upwardly. In the case of the trapezoidal cross section shape shown in FIG. 5(a), for example, arrangement may be such that the height h is 1 to 3 mm, the bottom surface width t1 is 1 to 3 mm, and the upper surface width t2 is 0.5 to 2.5 mm. The guide groove may be formed in accordance with this shape. Also the size of guide projection in a longitudinal direction (circumferential direction) may be conveniently made shorter than the opening length of the flange insertion groove while keeping it within a range in which an upward floating up is effectively prevented when the syringe is mounted. For example, for a syringe barrel with an outer diameter of 30 to 40 mm, the size of guide projection in a longitudinal direction may be 20 to 120 degrees, and preferably 30 to 90 degrees in terms of angles taking the center of barrel as the center of angle.

Although the cross section is a trapezoid in this embodiment, it may be a square, a triangular, or etc.

Preferably, in the present invention, the rear surface of the flange is provided with a press projection. Also in the present invention, by providing a reinforcing rib on the rear surface of the flange, the breakage of the flange may further prevented.

Figure 8:
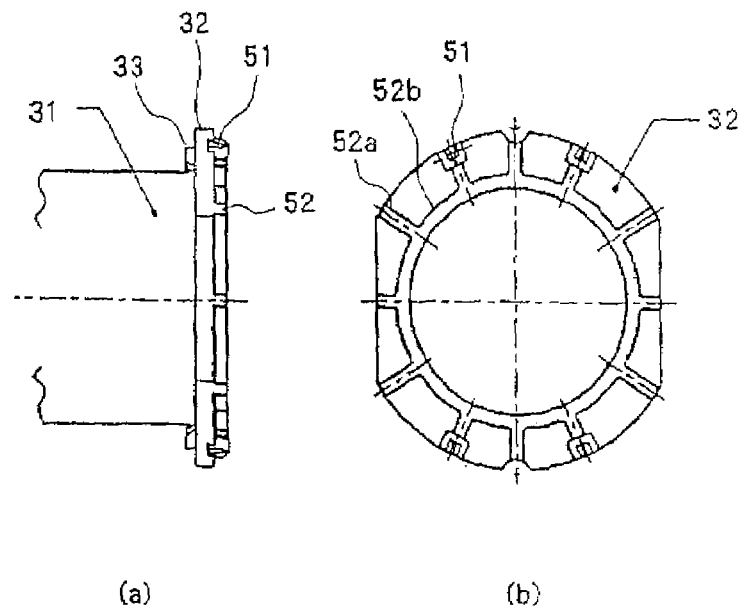
FIG. 8 shows an embodiment of the syringe of the present invention, wherein
 (a) is a side view of the syringe, and
 (b) is a rear view of the flange seen from rear side the syringe.
Figure 9:
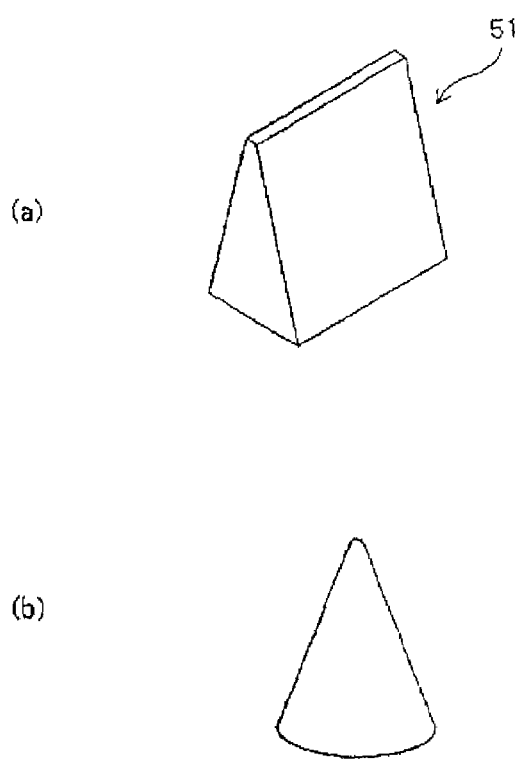
FIGS. 9(a) and (b) show examples of the press projection.

FIG. 8 shows an example of the flange 32 having press projections 51 and reinforcing ribs 52. When the flange is fitted in the use position by inserting it into the flange insert groove, the tip of the press projection is compressed generating elastic force to press the flange forwardly, and thus the flange is firmly secured. As shown in FIG. 9(a), the press projection 51 preferably has a narrower width toward the tip to make it more easily deformed by being pressed. The outer cylinder of the syringe is generally formed of a resin such as polypropylene, and the adaptor is formed of ABS, polycarbonate, or the like. Depending on the selection of the material, the cylinder holder side may be arranged to be compressible. When the above described materials are used, the projection of the syringe barrel is compressed. At this moment, even if the tip of the projection undergoes plastic deformation by compression, a certain level of the compressive force is preserved and therefore the flange is firmly secured by the resiliency.

The shape and the height of the projection may be determined taking these materials into account. Generally, it is preferable to arrange such that the distance from the front surface of the flange to the tip of the press projection is larger than the width of the flange insert groove by about 0.1 to about 2.5 mm, more preferably about 0.2 to about 1.0 mm. The press projection may have a conical shape as shown in FIG. 9(b).

Figure 10:
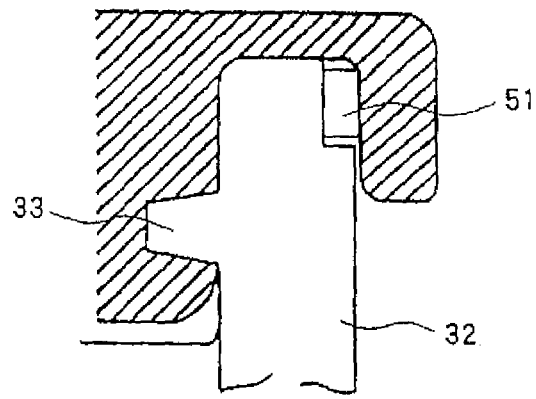
FIG. 10 shows the state in which a flange is inserted into a flange insert groove and fixed.

FIG. 10 shows the state in which the flange 32 is fitted in the flange groove. The press projection 51 has undergone deformation, thereby pressing the flange 32 against the front surface of the flange groove 14. The position of disposing the press projections 51 is, as shown in FIG. 8, preferably a position close to the back side of the guide projection 33 formed on the front surface of the flange.

There are no particular restrictions on the shape of the reinforcing ribs, and an example may include a combined shape of a concentric part 52b and a radial part 52a as shown in FIG. 8. In this example, since the press projections 51 are formed on the extension of the radial part, the radial part is deformed accordingly. The press projection may be arranged in other places.

Next, other embodiments of the guide projection will be shown.

Figure 11:
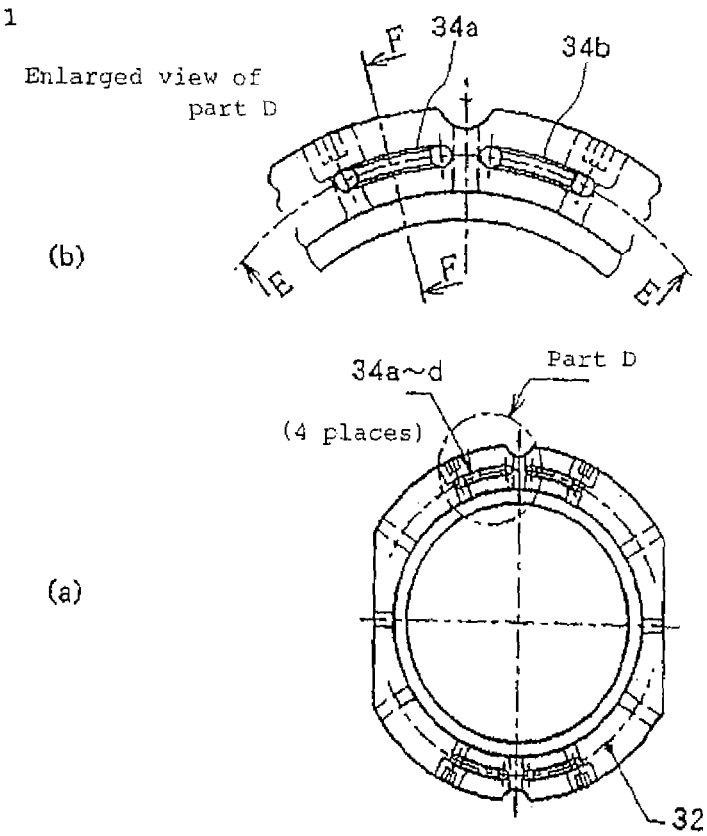
FIG. 11 is a front side view to show a flange surface of a different example of the syringe barrel, wherein
 (a) is a front view (whole view) of the flange, and
 (b) is an enlarged view of the part D of (a).

In the example shown in FIG. 11, a guide projection 34, which is shorter than the guide projection shown in FIG. 4, is formed in four places. As shown in the enlarged view of FIG. 11(b), the end-to-end distance including adjacent two guide projections 34a and 34b is preferably arranged in the same manner as the length of the guide projection 33 in the lengthwise direction shown in FIG. 4. The E-E cross sectional view is the same as the one in FIG. 5, and arrangement may be made in the same manner as the example of the guide projection of FIG. 4. In FIG. 11, an example is shown in which a press projection and reinforcing ribs are formed on the rear surface.

The guide projection may be of a plurality of truncated cones placed in a line in the circumferential direction; in which case, a plurality of truncated cones may be disposed at the positions where the guide projections of FIG. 4 are provided.

As described, in a preferable embodiment of the present invention, the number of the arcuate guide projections may be even number and each half number is symmetrically positioned on the flange where the two flange cut portions are not provided.

Figure 12:
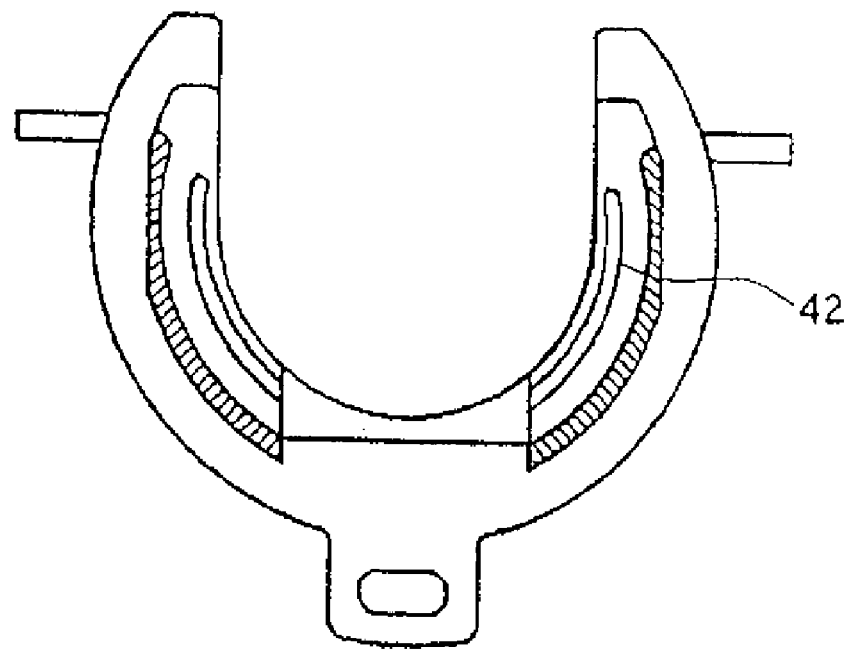
FIG. 12 shows a different example of the adaptor (a cross section corresponding to the A-A cross section of FIG. 2).
Figure 13:
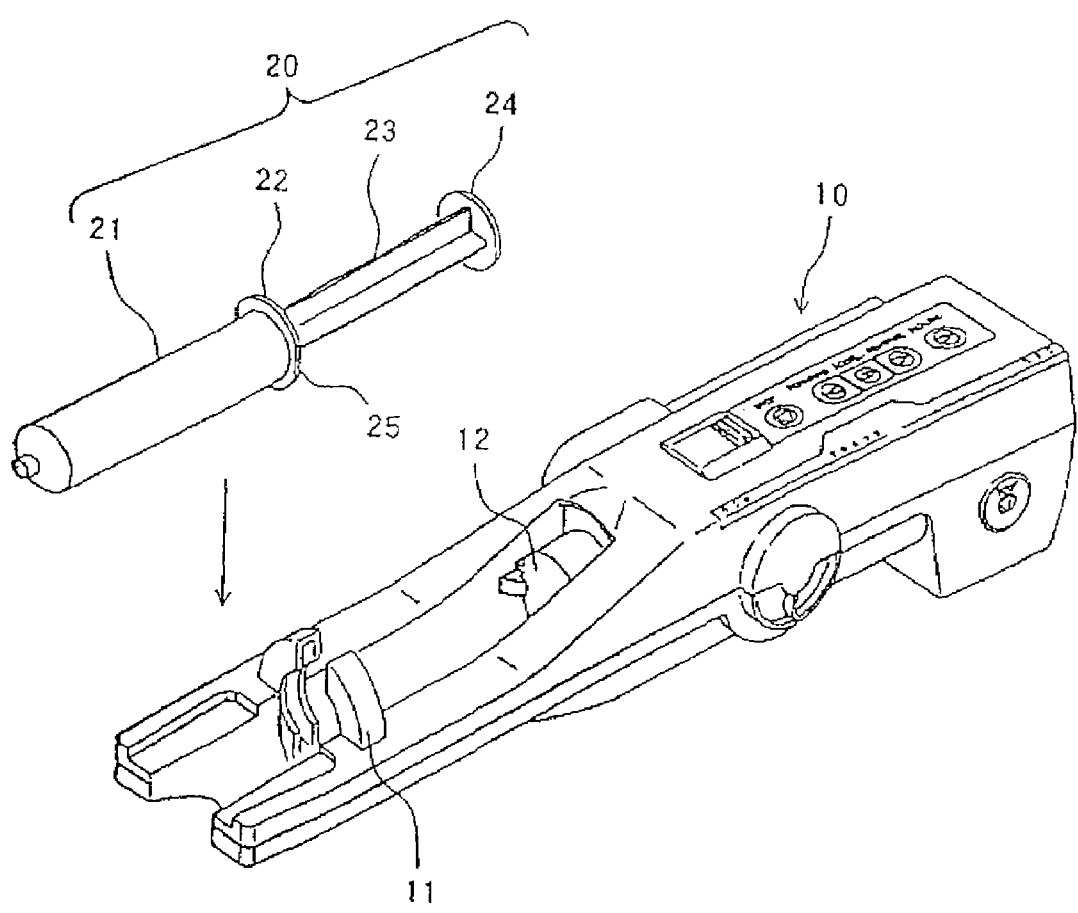
FIG. 13 shows a state of mounting a syringe on an automatic injection device.
Figure 14:
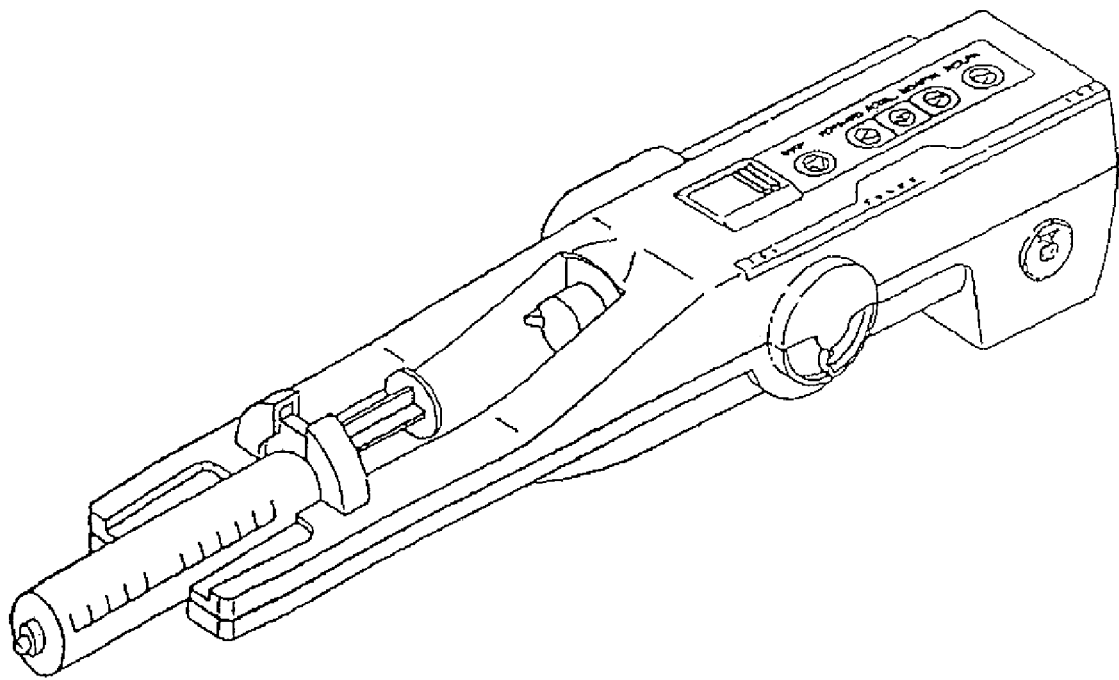
FIG. 14 shows a state of a syringe which is mounted on an automatic injection device.
Figure 15:
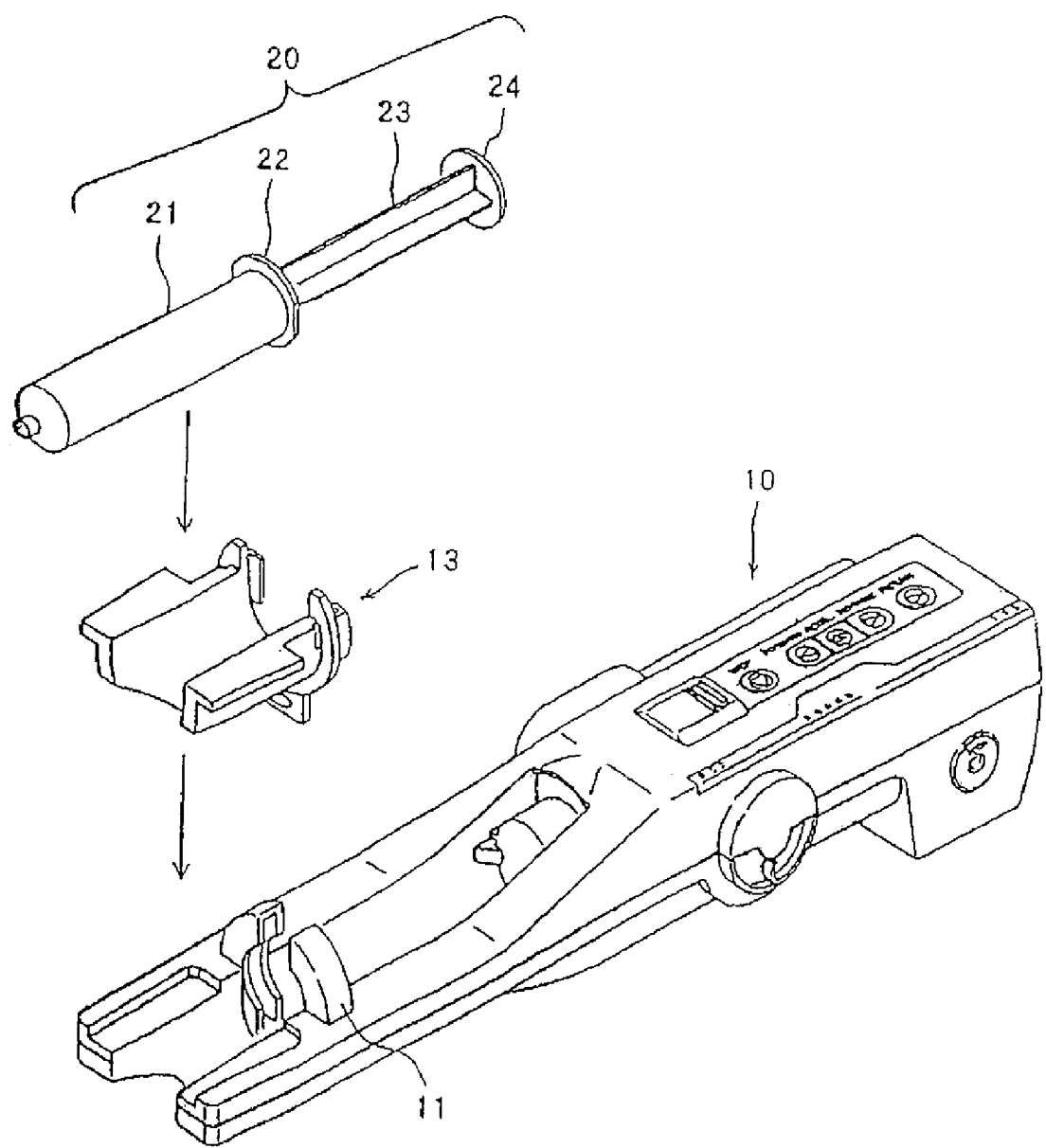
FIG. 15 shows a state of mounting a syringe on an automatic injection device using an adaptor.
Figure 16:
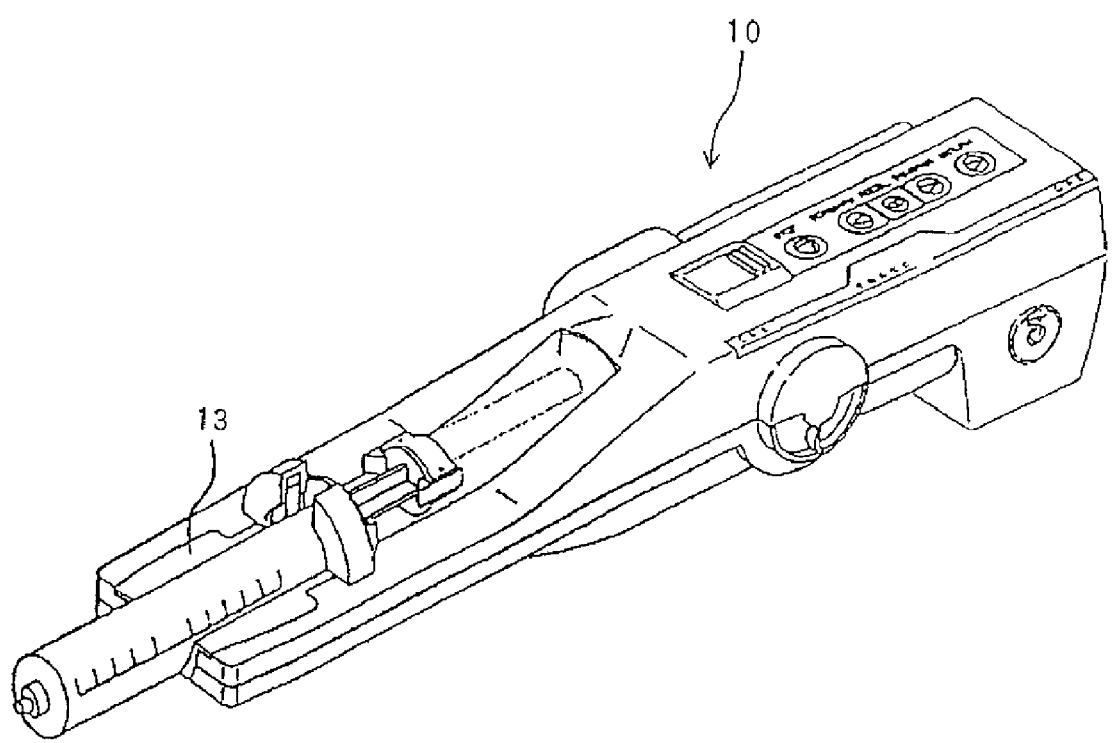
FIG. 16 shows a state of a syringe which is mounted on an automatic injection device.

Although, in the above described examples, the guide projection is formed on each side of the flange cut part (top and bottom in FIGS. 4 and 11), it may be formed on only one side. The guide groove of the adaptor to be used in combination with the guide projection may be open in the top part as with the guide groove 41 shown in FIG. 2 or closed as with the guide groove 42 shown in FIG. 12. When the top part is closed, the flange can be inserted into the adaptor keeping its guide projection down, and then be rotated until the use position is reached.

The above-described embodiment is one example of the present invention, and it should be noted that various changes can be made without departing from the scope of the present invention.

As described above, according to the present invention, there can be provided provide a syringe barrel a cylinder holder, where the syringe is not easily broken in injecting liquid of high viscosity at high pressure and can be easily mounted.

What is claimed is:

1. A solution injection system comprising:
   a mechanical syringe driving mechanism having a barrel holder with a flange insert groove and an arcuate guide groove formed on a front side wall surface of the flange insert groove; and
   a syringe having a syringe barrel comprising
      a barrel having a body configured to be received within said barrel holder and having a first end and a dispensing end opposite the first end,
      a flange extending outwardly from the barrel body proximate said first end and having an arcuate guide projection extending outwardly from a front surface of the flange towards the dispensing end,
      a press projection formed on the rear surface of the flange,
      a tip of the press projection being capable of being compressed to press the flange against a front sidewall surface of a flange insert groove when the flange is inserted into the flange insert groove formed in a cylinder holder and is fitted in a use position,
      wherein the arcuate guide projection is configured to engage with the guide groove of the barrel holder when the syringe barrel is inserted into the barrel holder, and
      wherein the press projection has a narrower width toward the tip, whereby the press projection is capable of being more deformed by being pressed.

2. A system according to claim 1, wherein the guide projection comprises two sections.

3. A system according to claim 1, wherein the flange has two flange cut parts symmetrically positioned in the flange opposite to each other.

4. A system according to claim 3, wherein an even number of the arcuate guide projections are provided so that each half number is positioned symmetrically to each other on the flange where the two flange cut parts are not provided.

5. A system according to claim 4, wherein the guide projections are arcuate in shape.

6. A system according to claim 5, wherein the arcuate guide projection comprises a plurality of guide projections aligned in a line in the circumferential direction on a front surface of the flange.

7. A system according to claim 6, wherein the flange has two flange cut portions symmetrically positioned in the rim of the flange opposite to each other.

8. A system according to claim 7, wherein an even number of the guide projections in the form of truncated cones are provided so that each half number is positioned symmetrically to each other on the flange where the two flange cut portions are not provided.

9. The solution injection system of claim 1, wherein the syringe is pre-filled with a chemical solution.

* * * * *